United States Patent [19]

Campbell et al.

[11] Patent Number: 4,785,005

[45] Date of Patent: Nov. 15, 1988

[54] 6-(6-ALKYLPYRIDONE)-CARBOSTYRIL COMPOUNDS AND THEIR CARDIOTONIC USES

[75] Inventors: Henry F. Campbell, Lansdale; Donald E. Kuhla, Doylestown; Bruce F. Molino, Lansdale; William L. Studt, Harleysville, all of Pa.

[73] Assignee: Rorer Pharmaceutical Corporation, Fort Washington, Pa.

[21] Appl. No.: 878,123

[22] Filed: Jun. 25, 1986

[51] Int. Cl.$^4$ .................. C07D 401/04; A61K 31/47
[52] U.S. Cl. .................................... 514/312; 546/158
[58] Field of Search ................ 514/312; 546/157, 158

[56] References Cited

U.S. PATENT DOCUMENTS 4,591,591  5/1986  Robertson ............................ 514/254
4,710,507  12/1987  Campbell et al. .................... 546/157

FOREIGN PATENT DOCUMENTS 148623  7/1985  European Pat. Off. ............ 546/157
155798  9/1985  European Pat. Off. ............ 544/238
8102575  9/1981  World Int. Prop. O. .
8400756  3/1984  World Int. Prop. O. .

OTHER PUBLICATIONS

"Medicinal Chemistry", by Alfred Burger (Ed.), Interscience Publishers, New York (1960) p. 42.

*Primary Examiner*—Donald G. Daus
*Assistant Examiner*—E. Bernhardt
*Attorney, Agent, or Firm*—James A. Nicholson; Alexis Barron; Martin F. Savitzky

[57] ABSTRACT

This invention relates to 6-pyridone-carbostyril compounds, uses of said compounds, including methods for increasing cardiac contractility, pharmaceutical compositions including the same and methods for the preparation thereof.

6 Claims, No Drawings

6-(6-ALKYLPYRIDONE)-CARBOSTYRIL COMPOUNDS AND THEIR CARDIOTONIC USES

FIELD OF THE INVENTION

This invention relates to novel carbostyril pyridones which possess useful cardiotonic properties. This invention relates also the uses of said compounds including methods for increasing cardiac contractility, which can be used, for example, for the treatment of congestive heart failure, pharmaceutical compositions including the same and methods for the preparation thereof.

Congestive heart failure is a life-threatening condition in which myocardial contractility is depressedso that the heart is unable to pump adequate amounts of blood to meet the body's metabolic needs. The leading causes for heart failure are believed to be an inadequate oxygen supply to the heart muscle or cardiomyopathy, a disorder or abnormality in the heart muscle tissue. As cardiac output decreases, other neurological mechanisms are activated, causing arterial and venous constriction, the redistribution of tissue blood flow and an increase in circulatory blood volume. As the condition worsens, the patient experiences edema, increased h eart size, increased myocardial wall tension, and eventually the heart stops pumping.

REPORTED DEVELOPMENTS

Drugs which increase the tone of the heart muscle are described as having positive inotropic activity and are characterized as cardiotonic agents. Digitalis glycosides have long been used to increase myocardial contractility and reverse the detrimental changes seen in congestive heart failure. More recently, dopamine, dobutamine, amrinone and milrinone have been used to provide necessary inotropic support for the failing heart.

Cardiotonic agents which are described as having positive inotropic activity includethe 5-pyridyl substituted pyridones disclosed in U.S. Pat. Nos.: 4,004,012; 4,072,746; 4,107,315; 4,137,233; 4,199,586; 4,271,168; and 4,107,315; in GB No. 2070606A; and in PCT published Appl. No. PCT/CH81/00023. Other cardiotonic drugs include the diazacyclic substituted carbostyril compounds disclosed in U.S. Pat. Nos. 4,414,390 and 4,415,572, cardiotonic pyridyl substituted carbostyril compounds disclosed in EPO application Serial No. 84308925.1, and the 5-phenyl-thiazole compounds disclosed in U.S. Pat. No. 4,418,070.

Cardiotonic bicyclic heteroaryl-5-substituted pyridyl compounds are disclosed in PCT published application Serial No. PCT/US83/01285; and, cardiotonic diazaheterocyclic-5-substituted pyridyl compounds are disclosed in U.S. Pat. Nos. 4,432,979, 4,514,400 and 4,539,321. Each of the aforementioned is assigned to the same assignee as the present application.

SUMMARY OF THE INVENTION

The present invention relates to carbostyril compounds substituted in the 6-position with a 5-[6-alkyl-pyrid-2-one] group, preferably dihydrocarbostyril compounds having such substitution, such as those described by the formula

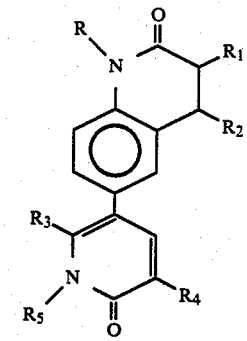

wherein:
$R$, $R_1$, $R_2$, $R_3$ and $R_5$ are each independently H or alkyl;
$R_4$ is alkyl, alkoxyalkyl, hydroxyalkyl, cyano, carbamoyl, alkyl carbamoyl, formyl, alkyleneamino or amino; or a pharmaceutically acceptable salt thereof.
It has been found that compounds within the scope of the present invention possess surprising and unexpected positive inotropic activity.

This invention relates also to pharmaceutical compositions which are effective in increasing cardiac contractility in humans and other animals and which are useful for the treatment of cardiac failure such as congestive heart failure.

DETAILED DESCRIPTION

Certain of the compounds encompassed within the scope of the present invention, and particularly, compounds of the above formula, may exist in enolic or tautomeric forms. All of such forms are considered as being included within the scope of this invention.

The compounds of this invention may be useful in the form of the free base, in the form of salts, and as a hydrate. All of such forms are considered as being within the scope of this invention.

Acid addition salts are a convenient form for use. In practice, use of the salt form inherently amounts to use of the base form. Acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial cardiotonic properties inherent in the free base are not vitiated by side effects ascribable to the anions. Although pharmaceutically acceptable salts of said basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures.

Examples of pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like. The corresponding acid addition salts comprise the following: hydrochloride, sulfate, phosphate, sulfamate, acetate, citrate, lactate, tartrate, malonate, methanesulfonate, ethanesulfonate, benzenesulfonate, p-toluenesulfonate, cyclohexylsulfamate and quinate, respectively.

The acid addition salts of the compounds of this invention can be prepared either by dissolving the free base in an aqueous or aqueous-alcohol solution or other suitable solvent(s) containing the appropriate acid and isolating the salt by evaporating the solution, or by reacting the free base and acid in an organic solvent, in which case the salt separates directly or can be obtained by concentration of the solution.

As employed above and throughout the disclosure, the following terms, unless otherwise indicated, shall be understood to have the following meanings:

"Alkyl" means a saturated aliphatic hydrocarbon which may be either straight- or branched-chained containing from about one to about six carbon atoms.

"Lower alkyl" means an alkyl group as above, having one to about four carbon atoms.

"Alkyl carbamoyl" means a carbamoyl group substituted by one or two alkyl groups. Preferred groups are the lower alkyl carbamoyl groups.

"Hydroxyalkyl" means an alkyl group substituted by a hydroxy group. Hydroxy lower alkyl groups are preferred and include hydroxymethyl, 2-hydroxyethyl, 2-hydroxypropyl, and 3-hydroxypropyl.

"Alkoxy" means an alkyl oxy group in which "alkyl" is as previously described. Lower alkoxy groups are preferred and include methoxy, ethoxy, n-propoxy, i-propoxy sec-propoxy, n-butoxy among others.

"Alkoxyalkyl" means an alkyl group as previously described substituted by an alkoxy group as previously described.

"Alkyleneamino" means —RNH$_2$ where —R is alkylene of one to about six carbon atoms. The preferred groups are the lower alkyleneamino groups which mean amino groups substituted with alkylene groups of one to about four carbon atoms. The most preferred alkyleneamino group is methyleneamino.

A preferred embodiment of the present invention includes those compounds which have a cyano group as the R$_4$ substituent group.

Particularly preferred compounds are those described by the formula

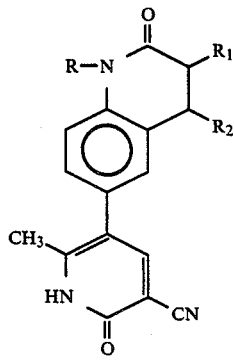

wherein R, R$_1$, and R$_2$ are each independently H or lower alkyl.

The most preferred embodiment of the present invention comprises the compound 6-[3'-cyano-6'-methyl-2'-oxo(1H)pyridin-5'-yl]-3,4-dihydrocarbostyril or a pharmaceutically acceptable salt thereof, that is

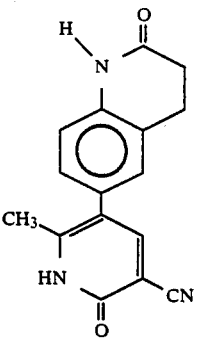

Compounds within the scope of the present invention may be prepared in accordance with the following reaction sequence.

The bicyclic portion of the compound can be prepared from aniline or a substituted aniline, as starting material, compounds which are generally commercially available or which can be readily prepared according to methods known in the literature. N-acylation of the aniline starting material with an acylating agent, for example, a beta-haloalkyl acyl chloride, results in an N-[beta-haloalkylacyl] aniline intermediate. The bicyclic 3,4-dihydrocarbostyril intermediate results from the cyclization of the N-acyl intermediate under Freidel-Crafts conditions with a Lewis acid such as aluminum chloride. To obtain compounds wherein R is other than hydrogen, either the starting material can be N-substituted or N-alkylation of the carbostyril nitrogen may be effected at this or a later step of the synthetic sequence.

The pyridone substituent is introduced into the position para to the carbostyril nitrogen by treating the carbostyril intermediate with an alpha-halo-acyl chloride to effect the desired electrophilic aromatic substitution. The resulting alpha-haloalkyl, carbostyril ketone intermediate is treated with an acetate anion and the keto groups is reduced to form the hydroxy compound. Dehydration and hydrolysis result in the carbonyl intermediate which is condensed with the dimethyl acetal of dimethylformamide. During the condensation, generated methanol is removed as the enamine condensation product is formed. Treatment of the enamine intermediate with the metal anion of R$_4$-substituted acetamide results in the cyclized pyridone product.

Treatment of the 1-(H)-pyridone with a suitable alkylating agent results in the compounds of the present invention wherein R$_5$ is other than hydrogen. When R$_4$ is cyano in the above formula, 2-cyano acetamide is used in the synthetic sequence above. Conversion of the cyano group into the other R$_4$ substituent groups may be accomplished by techniques known in the art.

The compounds of this invention can be normally administered orally or parenterally, in the treatment of cardiac disorders such as heart failure in humans or other mammals.

The compounds of this invention, preferably in the form of a salt, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Suitable carriers include diluents or fillers, sterile aqueous media and various non-toxic organic solvents. The compositions may be formulated in the form of tablets, capsules, lozenges, trochees, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of inotropic active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers.

Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in aqueous alcoholic media or in sesame or peanut oil or aqueous solutions of the soluble pharmaceutically acceptable salts described herein can be employed. Solutions of the salts of these compounds are especially suited for intramuscular and subcutaneous injection purposes. The aqueous compositions, including solutions of the salts dissolved in pure distilled water, are also useful for intravenous injection purposes, provided that their pH is properly adjusted, suitably buffered, made isotonic with sufficient saline or glucose and sterilized by heating or by microfiltration. Certain compositions useful for intravenous injection or infusion may be prepared using the solid form of the active compound of the present invention. The solid compound may be suspended in propylene glycol, or a polyethylene glycol ether such as PEG 200, using a sonicator and the resulting mixture combined with aqueous media.

The dosage regimen in carrying out the methods of this invention is that which insures maximum therapeutic response until improvement is obtained and thereafter the minimum effective level which gives relief. Thus, in general, the dosages are those that are therapeutically effective in increasing the contractile force of the heart or in the treatment of cardiac failure. Exemplary of such doses are an oral dose which may be between about 0.001 mg/kg and about 30 mg/kg (preferably in the range of 0.001 to about 10 mg/kg), and the i.v. dose of about 0.001 to about 10 mg/kg (preferably in the range of 0.001 to about 3 mg/kg). It should be borne in mind that, in selecting the appropriate dosage in any specific case, consideration must be given to the patient's weight, general health, age and other factors which may influence response to the drug. The drug may be administered as frequently as is necessary to achieve and sustain the desired therapeutic response. Some patients may respond quickly to a relatively large or small dose and require little or no maintenance dosage. On the other hand, other patients may require sustained dosing from about one to about four times a day depending on the physiological needs of the particular patient. It is anticipated that many patients will require no more than about one to about two doses daily.

It is also anticipated that the present invention would be useful as an injectable dosage form which may be administered in an emergency to a patient suffering from acute cardiac failure. Such treatment may be followed by intravenous infusion of the active compound and the amount of compound infused into such patient should be effective to achieve and maintain the desired therapeutic response.

EXAMPLES

The following is an exemplary preparation of one compound of the present invention.

EXAMPLE 1

The Preparation of 6-[3'-Cyano-6'-methyl-2'-oxo(1H)pyridin-5'-yl]-3,4-dihydrocarbostyril Step 1. 6-[α-Acetoxy-propionyl]-3,4-dihydrocarbostyril A mixture of 1-bromoethyl-6-[3,4-dihydrocarbostyril] ketone (5 g), potassium acetate (7 g) and glacial acetic acid (50 ml) is refluxed for five hours. The reaction mixture is diluted with water and extracted with chloroform, and the combined organic layers are washed with saturated aqueous sodium bicarbonate, dried, filtered and concentrated to afford the desired product as a solid which is used in the next step without further purification.

Step 2. 6-[2-Acetoxy-1-hydroxypropyl]-3,4-dihydrocarbostyril

Sodium borohydride (4.6 g) is added slowly to a stirred solution of the α-acetoxy ketone (20 g) prepared in Step 1. above and a mixture of glacial acetic acid (26 ml) and diglyme (300 ml) maintained at a temperature of about 10°–15° C. The reaction mixture is stirred for an additional hour, cooled to 0° C., quenched with water and extracted with ethyl acetate. The organic extent is washed with saturated aqueous sodium bicarbonate, dried, filtered and concentrated by vacuum distillation affording the desired product as a gum which is used in the next step without further purification.

Step 3. 6-(2-Oxopropyl)-3,4-dihydrocarbostyril

A mixture of the acetoxy compound prepared in Step 2. above (11.8 g) and potassium bisulfate (15 g) and 18-crown-6-ether (0.6 g) in diglyme (250 ml) is stirred at 115°–135° for about 1.5 hours, cooled to room temperature and diluted with water. The aqueous mixture is extracted with ethyl acetate. The organic extract is washed with saturated sodium bicarbonate, saturated aqueous sodium chloride, dried, filtered and evaporated in vacuo. The solid residue is triturated in ethyl acetate and hexane, and the wet solid dried, this affording the desired product as a solid, M.P.=136°–138° C.

Step 4. 6-[2-(1-Dimethylamino-3-oxo-butene-2-yl)]-3,4-dihydrocarbostyril

A mixture of the oxo compound obtained in Step 3. above (750 mg), dimethyl formamide dimethyl acetal (5 ml) and pyridine (0.3 ml) stirred under nitrogen at a temperature of 75°–80° C. for about 22 hours. The reaction mixture is cooled to 0° C., filtered and the resulting precipitate rinsedwith cold ethyl ether and dried in vacuo, this affording the desired crude product as a solid, M.P.=178°–180° C.

Step 5. 6-[3'-Cyano-6'-methyl-2'-oxo(1H)pyridin-5'-yl]-3,4-dihydrocarbostyril

A mixture of the dimethylamino compound obtained in Step 4. (740 mg), 2-cyanoacetamide (278 mg), sodium hydride (oil-free) (144 mg) and anhydrous DMF (10 ml) is stirred under nitrogen and maintained at a temperature of 75°–80° C. for about 5.5 hours and stirred overnight at room temperature. Saturated ammonium chloride solution (70 ml) is added to the reaction mixture which is cooled to 0° C. The mixture is filtered, the filtered solid washed with water and dried overnight in vacuo affording a crude solid which is recrystallized using warm DMF and a mixture of methylene chloride and hexanes, this affording the desired product as a solid M.P.>350° C.(dec).

The compounds of Formula I possess positive inotropic activity and are useful as cardiotonic agents in the treatment of humans and other animals, particularly other mammals for cardiac disorders including congestive heart failure. The effectiveness of the compounds of this invention as inotropic agents may be determined by the following pharmacologic tests which evaluate the change in cardiac contractile force upon exposure to a dose of said compounds. The anesthesized dog procedure is a standard test procedure; the inotropic results of this procedure generally correlate with the inotropic activity found in human patients.

Ganglionic-Beta Blocked Anesthetized Dog Procedure

Adult mongrel dogs of either sex weighing 10 to 16 kg are fasted overnight, anesthetized with pentobarbital sodium 35 mg/kg, i.v. intubated, respired with room air using a Harvard respirator, and instrumented surgically to monitor myocardial contractile force, heart rate, arterial pressure, aortic flow and EKG limb lead II. The aforesaid measurements are recorded continously on a strip chart recorder.

Myocardial contractile force is monitored by a a Walton-Brodie strain gauge sutured to the left ventricular myocardium parallel to the left anterior descending coronary artery. Arterial pressure is measured using a fluid-filled catheter attached to a pressure transducer introduced via the right femoral artery and positioned in the thoracic aorta. Mean arterial pressure is determined by electronically clamping the pulsatile pressure signal. Aortic flow is monitored using a precalibrated, noncannulating electromagnetic flow probe positioned around the thoracic aorta. Heart rate is monitored using a cardiotachometer triggered by the QRS complex of the limb lead II EKG. The right femoral vein is cannulated for intravenous infusion of drugs. Body temperature is maintained at 37±1° C.

Following a 30 min postsurgical stabilization period, control values are recorded. Myocardial depression is induced by ganglionic and beta receptor blockade. Initially, the responsiveness of the autonomic nervous system is assessed by performing a 30 sec bilateral carotid occlusion (BCO). Ten minutes later, a saline solution of isoproterenol 0.3 mcg/kg i.v. is administered to assess beta receptor integrity. Ten minutes after that, a saline solution of mecamylamine 2 mg/kg i.v. is infused, followed by a saline solution of propranolol 1 mg/kg i.v. plus 0.3 mg/kg/hr. Twenty five minutes later, a second BCO is performed to demonstrate ganglionic blockade followed by a send injection of saline isoproterenol 0.3 mcg/kg i.v. to demonstrate beta blockage. Ten minutes later, the test compound or vehicle is administered intravenously in ascending doses at 30 min intervals at 1.5 ml/ml in a total volume of 3.5 ml. On completion of the experiment, both BCO and isoproterenol challenges are repeated to verify ganglionic and beta blockade.

The results of the blocked dog test show that compounds of the present invention increase contractile force and aortic blood flow in a dose-related manner while maintaining arterial pressure and having minimal effects on heart rate.

Comparative Test Results

Solutions of the most preferred compound of the present invention, 6-[3'-cyano-6'-methyl-2'-oxo(1H)pyridin-5'-yl]-3,4-dihydrocarbostyril, and milrinone, 3-cyano-6-methyl-5-(4-pyridyl)-pyridin-2-one, were administered intravenously in accordance with the procedure described above. The solutions were prepared by dissolution in PEG 200 followed by serial saline dilution to yield test doses. Test solutions of 6-[3'-cyano-6'-methyl-2'-oxo(1H)pyridin-5'-yl]-3,4-dihydrocarbostyril were prepared at doses of 3, 10 and 30 mcg (expressed as base) per kg, and solutions of milrinone were prepared at test doses of 30, 100 and 300 mcg/kg.

The compound, 6-[3'-cyano-6'-methyl-2'-oxo(1H)pyridin-5'-yl]-3,4-dihydrocarbostyril, increases contractile force to a maximum of 97% and heart rate 17% at a dose of 30 mcg/kg i.v., and aortic blood flow to a maximum of 51%. Arterial blood pressure is not altered at the doses tested. In contrast, milrinone increases contractile force 111% and heart rate 19% at a dose of 100 mcg/kg i.v., and aortic blood flow only transiently at low dose. Milrinone decreased the mean arterial pressure in a dose-related sustained manner with a maximum decrease of 32%.

The inotropic $ED_{50}$ for 6-[3'-cyano-6'-methyl-2'-oxo(1H)-pyridin-5'-yl]-3,4-dihydrocarbostyril and milrinone are 16 and 50 mcg/kg i.v. respectively.

Additional test procedures which have been found to be an efficient means for ascertaining the inotropic activity of the compounds of this invention are described below.

The following test procedure is a standard test for determining the oral activity of the present compounds.

Conscious Instrumented Dog

Mongrel dogs (10–18.5 kg) are anesthetized with sodium pentobarbital (35 mg/kg i.v., supplemented as necessary during surgery) intubated and connected to a Harvard respirator. The left side of the chest is opened at the fifth intercostal space, and a Konigsberg transducer inserted into the left ventricle through a puncture at the apex and secured. A fluid-filled polyethylene catheter is inserted into the left atrium through a puncture wound and secured for measurement of left atrial pressure. A second fluid-filled catheter is inserted into the aorta for measurement of blood pressure and heart rate and secured to the vessel wall. The two catheters and the Konigsberg transducer cable are passed out of the chest through the seventh intercostal space and advanced subcutaneously to the back of the neck and passed through the skin. The fluid-filled catheters are filled with heparinized 50% dextrose solution, and the chest is closed and evacuated.

The dogs are treated daily post-operatively with 600,000 units of penicillin-procaine i.m. for ten days and with chloramphenicol, 500 mg/kg i.m., every other day for 10 days and allowed at least 7 days recovery before use.

Each dog is trained and acclimated to her environment and the presence of personnel during the experiment.

The following in vitro method is another means for measuring the inotropic potency of the present compounds. This method is a modification of the enzyme inhibition method reported by Thompson, W. J. and Appleman, M. M., "Characterization of Cyclic Nucleotide Phosphodiesterase of Rat Tissue," J. Biological Chemistry, Vol. 246, pp. 3145–3150 (1971); and Thompson, W. J., Brooker, G. and Appleman, M. M., "Assay of Cyclic Nucleotide Phosphodiesterase with Radioactive Substrates," Methods in Enzymology, Vol. 38, pp. 205–212 (1974); and is believed to correlate to in vivo intropic activity in humans.

Inhibition of Peak III cAMP Phosphodiesterase Activity

The test compounds are included in media comprising a radioactively labeled substrate ($^3$H-cyclic nucleotide) such as adenosine 3':5'-monophosphate (cyclic AMP) and guanosine-3':5'-monophosphate(cyclic GMP), and a non-rate-limiting amount of 5'-nucleotidease isolated from a dog heart. The inhibition of the enzyme hydrolysis of the 5'-nucleotide product of the cNUC-PDEase to the corresponding nucleoside is measured by separating the charged, unhydrolyzed substrate from the uncharged hydrolysis product. Separation may be acheived either chromatographically from the uncharged nucleoside product of the assay with ion-exchange resin or preferentially quenched with the ion-exchange resin so that it is not quantitated with the liquid scintillation counter.

Compounds of the present invention possess surprising and unexpected Peak III phosphodiesterase inhibiting activity. Results of this assay indicate that 6-[3'-cyano-6'-methyl-2'-oxo(1H)pyridin-5'-yl]-3,4-dihydrocarbostyril is about twelve times more potent than milrinone.

We claim:
1. A compound of the formula

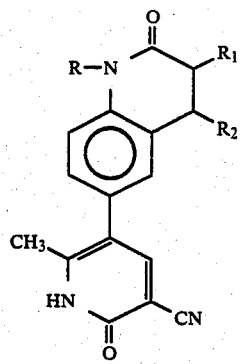

wherein:
R, $R_1$ and $R_2$ are each independently H or lower alkyl; or a pharmaceutically acceptable salt thereof.

2. 6-[3'-Cyano-6'-methyl-2'-oxo(1H)pyridin-5'-yl]-3,4-dihydrocarbostyril or a pharmaceutically acceptable salt thereof.

3. A method for increasing cardiac contractility in a human or other animal requiring such treatment which comprises administering thereto an effective inotropic amount of a compound according to claim 1.

4. A pharmaceutical composition for increasing cardiac contractility in a human or other animal requiring such treatment comprising an effective inotropic amount of a compound according to claim 1 in admixture with a pharmaceutically acceptable carrier.

5. A method for increasing cardiac contractility in a human or other animal requiring such treatment which comprises administering thereto a composition comprising an effective inotropic amount of 6-[3'-cyano-6'-methyl-2'-oxo(1H)pyridin-5'-yl]-3,4-dihydrocarbostyril or a pharmaceutically acceptable salt thereof.

6. A pharmaceutical composition for increasing cardiac contractility in a human or other animal requiring such treatment comprising an effective inotropic amount of 6-[3'-cyano-6'-methyl-2'-oxo(1H)pyridin-5'-yl]-3,4-dihydrocarbostyril or a pharmaceutically acceptable salt thereof in admixture with a pharmaceutically acceptable carrier.

* * * * *